United States Patent [19]

Polne-Fuller

[11] Patent Number: 5,051,365

[45] Date of Patent: Sep. 24, 1991

[54] MICROORGANISMS AND METHODS FOR DEGRADING PLANT CELL WALLS AND COMPLEX HYDROCARBONS

[75] Inventor: Miriam Polne-Fuller, Santa Barbara, Calif.

[73] Assignee: The Regents of the University of California, Berkeley, Calif.

[21] Appl. No.: 43,219

[22] Filed: Apr. 27, 1987

[51] Int. Cl.$^5$ .......................... C12N 9/14; C12N 1/10; C12N 1/22; C12N 1/26
[52] U.S. Cl. .................................. 435/264; 435/243; 435/248; 435/252; 435/258; 435/267; 435/277; 435/947; 435/172.1; 435/195; 435/200
[58] Field of Search ............... 435/243, 248, 252, 258, 435/267, 277, 947, 172.1, 264, 195, 200, 262

[56] References Cited

PUBLICATIONS

Frank, H. K., CA104:126209e, pp. 366–367 (1986).
Preston, J. F. III et al., CA:103:39729q, p. 147 (1985).
Steadman, T. L., *Stedman's Medical Dictionary*, pp. 344 and 712, (1982).
Nakada, H. I., et al., J. Biol. Chem., vol. 242, No. 5, pp. 845–851, (1967).

*Primary Examiner*—Esther L. Kepplinger
*Assistant Examiner*—Toni Scheiner
*Attorney, Agent, or Firm*—Pretty, Schroeder, Brueggemann & Clark

[57] ABSTRACT

Unique marine amoebae capable of digesting algal cell walls and degrading complex hydrocarbons, including plastics, and methods for treating algae and complex hoydrocarbons using the amoebae and partially purified enzymes from the amoebae.

11 Claims, 1 Drawing Sheet

MICROORGANISMS AND METHODS FOR DEGRADING PLANT CELL WALLS AND COMPLEX HYDROCARBONS

GOVERNMENT SUPPORT

This invention was made with Government support under Grant No.: DCB 85-10326 with the National Science Foundation and the University of California. The Government has certain rights in this invention.

FIELD OF THE INVENTION

This invention relates to novel microorganisms, particularly to protozoan amoebae which are capable of degrading seaweed cell walls and plastics, and to methods for treating seaweed and plastics utilizing such amoebae.

BACKGROUND OF THE INVENTION

Algae, including red, brown and green algae commonly known as seaweeds, are the primary producers of the marine environment which covers approximately 70% of the earth's surface. In addition, seaweeds yield unique biochemical substances which may be pharmacologically active, for example as viral inhibitors or cell division inhibitors, and substances which can serve as jelling and thickening agents. Cell walls which encase the cell body of algae and higher plants, create obstacles to the use of plant cells in procedures such as the introduction of foreign DNA for transformation into the cells, and somatic hybridization in which sexually unrelated cells may be united to create a new, combined genome.

Protoplasts, which are cells with the cell wall removed, are thus useful for various genetic manipulations of the plant cell, including those which may be used to attempt to improve the characteristics of the whole plant. In particular, seaweed protoplasts may provide a means to study the basic biology of algal cells including cell physiology, biochemistry, cell wall development and plant differentiation, and may be useful in seaweed cultivation (aquaculture). It has been particularly difficult to isolate protoplasts from seaweeds due to the nature of the cell wall which is composed largely of complex sulphated polysaccharides, and because of the commercial unavailability of enzymes effective in degrading these complex molecules. In general, attempts to isolate protoplasts from higher plants have used techniques where the plant is cleaned and sectioned then placed in solutions containing fungal or bacterial enzymes for several hours. Released protoplasts are collected using density gradients or by the use of separating devices such as nylon screens. In other procedures, soft seaweed tissues are treated with sea snail intestinal enzymes and have been ground to release protoplasts using a tissue homogenizer. These methods are inefficient and tedious, yielding low numbers of protoplasts, many of which are damaged by the procedure used to obtain them.

Microorganisms which can efficiently digest cell walls, would thus be highly useful.

Pollution of the ocean with plastic wastes, particularly those materials composed of complex hydrocarbons, including halogenated hydrocarbons, causes harm to marine life, which if not controlled, may rise to the level of that caused by oil spills and toxic chemical waste. While plastics, which are generally not biodegradable, are fast replacing biodegradable natural packaging materials, there has not been a corresponding development of methods for degrading plastic. Thus the accumulation of plastic wastes poses a continuing problem. In addition, the plastic manufacturing industry produces a variety of by-products during the production of plastics including polyvinyl chloride and polyvinylidin di-chloride, which must then be disposed of. There is a need for a method to degrade these by-products rather than introducing them into the environment where they may contribute to the pollution problem.

Biological processes are being increasingly employed in industry to combat pollution. In particular, microorganisms are being developed to degrade pollutants. It would therefore be advantageous to develop microorganisms capable of degrading plastics.

SUMMARY OF THE INVENTION

Accordingly, the present invention provides amoebae which digest seaweed cell walls. One of the amoebae, AM-I-7PL is also capable of degrading complex hydrocarbons. Both amoebae may be used to remove cell walls to generate seaweed protoplasts. AM-I-7PL may be incorporated into a process to treat complex hydrocarbons, such as plastics and plastic by-products.

BRIEF DESCRIPTION OF THE DRAWINGS

The details of typical embodiments of the present invention will be described in connection with accompanying drawings in which.

DETAILED DESCRIPTION OF THE INVENTION

Figure 1:
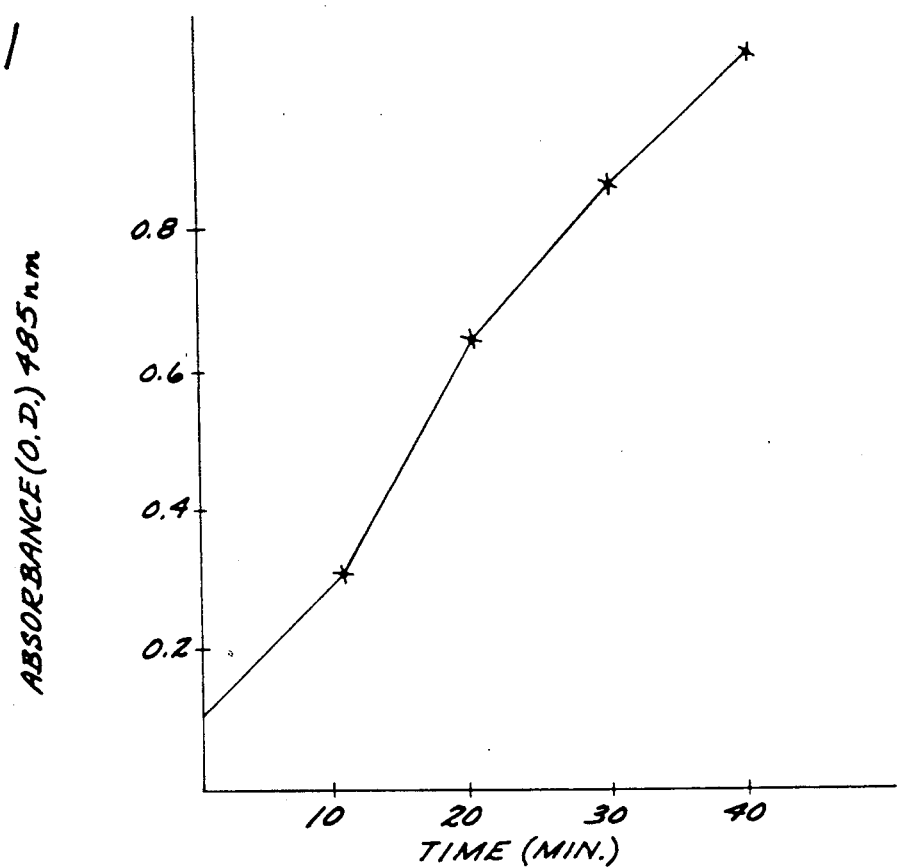
FIG. 1 is a graph depicting the change in absorbance over time during Anthron reactions using the partially purified enzyme mixture obtained from the amoeba AM-I-7wt of the invention.

Amoebae are a diverse group of single-celled, usually microscopic, organisms of the phylum Protozoa which are typically found in seawater and fresh water, soil and in animals as parasites. Amoebae are generally of indefinite, changeable form and move by means of protrusion of their cytoplasm. Such protrusions are generally termed "pseudopodia" and serve both for locomotion and to surround and ingest food particles. Amoebae have widely varying morphological and ecological characteristics. Such characteristics may be used to distinguish the various genera and species of amoebae. For example amoebae may be identified by cell size; number and size of nuclei; shape of pseudopodia; presence or absence of external envelop or test; speed and sequence of motion; food sources and feeding behavior.

Most amoebae in the aquatic environment are believed to be associated with detritus and to feed on bacteria, decaying plant and animal matter or microscopic algae. One of the marine amoebae capable of digesting seaweed cell walls described herein was isolated from intact seaweed tissues as described below, and was found to florish on seaweed tissue as a sole food source, as demonstrated by its continued growth after the removal of debris and bacteria from the seaweed. This amoeba digests rapidly and completely a variety of algae including brown and red seaweeds and unicellular algae and was used to derive a mutant amoeba described below, which is also capable of digesting seaweed and in addition degrades complex hydrocarbons, including halogenated and chlorinated hydrocarbons such as polyvinyl chloride and polyvinylidin di-chloride.

The following examples are presented to illustrate the present invention and to assist one of ordinary skill in making and using the same. The examples are not intended in any way to otherwise limit the scope of the disclosure of the protection granted by Letters Patent hereon.

EXAMPLE I

Isolation of A Seaweed-digesting Amoeba

A biologically pure multinucleated amoeba, herein termed AM-I-7wt, capable of digesting seaweed cell walls was isolated in small numbers from stipes of young plants of the seaweed *Sargassum muticum* collected in January, 1984, from the rocky shores at Alegria Beach, Hollister Ranch, Santa Barbara County, Calif. Reproductive plants of Sargassum, which were also infected with amoeba, were collected at the same site in April, 1985. The plants were kept moist and stored at 5° C.

Since competing bacteria are detrimental to the amoebae and must be eliminated, the seaweed was partially cleaned with mild bleach or alcohol which eliminated most of the competing bacteria population on the seaweed surface. Sections of seaweed branches (1 to 2 cm long) were partially cleaned of surface microorganisms as described by Polne-Fuller et al., in: Seaweed Cultivation for Renewable Resources, (Bird and Benson, Eds.), *Gas Res. Inst.*, Chicago Ill. (1987), incorporated by reference herein. Briefly, cleaning was performed in chilled, sterile seawater (5° C.). The tissue was sonicated for 15 seconds for four times in an L & R Sonicator at setting "3" (Ultrasonic 320, Kearny, N.J.) using sterile seawater rinses between each sonication. The tissues were then soaked in a 0.1% solution of bleach (5.25% sodium hypochlorite by weight) or 30% ethanol for 2 minutes with gentle agitation. The tissue was rinsed using chilled, sterile seawater and incubated in an antibiotic mixture containing streptomycin sulfate, 0.2%, penicillin-G (0.1%), neomycin (0.2%) nystatin (0.0015%) and kanamycin (0.1%) for three days. Sections (2 to 5 mm) of the antibiotic-treated seaweed tissue were then placed on Provasoli Enriched Seawater (PES) medium containing seawater enriched with nitrogen-phosphorus vitamins and trace metals as described by Provasoli, in Culture and Collections of Algae, *Proc. U.S.-Japan Conf.*, Hakone, Japan (1966), incorporated herein by reference, solidified with 1.5% agar, and to which the same antibiotic mixture was added.

To obtain pure cultures of surviving amoebae, amoebae cells migrating on the surface of the agar were axenically cloned. This procedure permits a determination of whether amoebae were degrading the seaweed, or whether bacteria associated with the amoebae were assisting in or responsible for the degradation of the seaweed. Thus, to ensure the absence of contaminating bacteria, the isolates were cultured initially on sterility test medium which contained 1.5% agar and PES medium enriched with 0.8% nutrient broth, 0.5% yeast extract and 0.2% sucrose. To prevent cell rupture or dessication, the cells were transferred from the agar surface by lifting each with a section of the agar, or by using a hair loop to which the cell was allowed to attach. Transfer of cells from the liquid cultures was performed using gentle pipetting, quickly removing cells to prevent their attachment to the pipette.

Amoebae which survived the cleaning treatment were then fed on seaweed, seaweed cell wall extracts, or unicellular algae as a sole food source. Growth was determined by measuring the number of cell divisions over time. Amoebae which were capable of surviving on seaweed as a sole food source were presumed to be capable of degrading the seaweed cell walls. The amoeba designated AM-I-7wt survived the cleaning treatment.

The ability of Am-I-7wt to degrade cell walls was initially indicated by its continued growth and subsequently by its ability to grow on commercial cell wall extracts of red and brown seaweeds. Degradation was also demonstrated by the disappearance of seaweed tissue or algal cells while the AM-I-7wt cultures continued to grow. In addition, visual inspection as well as light microscopy revealed the presence of particles of seaweed and algal cells within food vacuoles in the amoeba. Later investigation involved examination of the contents of the food vacuoles using the induction of multiple fission to obtain release of vacuole contents as described below.

A culture of AM-I-7wt has been deposited in the American Type Culture Collection (ATCC) (Rockville, Md.) and has received accession number ATCC 40318.

EXAMPLE II

Characterization of AM-I-7wt

Cultures of AM-I-7wt were further evaluated to determine optimal culture parameters, including salinity, pH and temperature. Observations of morphology were also made. An inverted Nikon microscope (No. 64077) was used for observations of cell morphology and movement at magnifications of from 100 to 1000 X. A Philips EM300 electrion microscope was used to observe the ultra-structure of the cytoplasm, nuclei, food vacuoles, cell membrane and cell test of the amoeba.

Staining of live AM-1-7wt cells was performed to characterize the nuclei, a distinctive feature of various amoebae. Live AM-I-7wt cells (more than 200 cells) were placed on a slide in a 0.01 $\mu$g/ml solution of 4'-6'-diamidino-2-phenylindole (DAPI stain, Sigma) in seawater. Alternatively, the cells were fixed in an acetic acid:ethanol solution (1:3) and then rinsed in fresh water before staining with DAPI, to store the cells for later experiments. A Reichart phase/epifluorescent microscope was used for fluorescent work to detect the fluoresence by the DAPI stain as described below. Acridine orange (0.01% dye in seawater) was also effective for staining the nuclei of AM-I-7wt The presence of acridine orange was indicated by yellow-green fluoresence under an ultra-violet light source.

Culture Parameters

AM-I-7wt grows well in seawater (both natural and artificial) having a salinity of from approximately 25 to 35 ppt, at a pH of from approximately 6.0 to 9.0 and at a temperature of from approximately 4° to 25° C., and is preferably cultured at 31 ppt salinity, pH 7.5, at 22° C.

Morphology

Observations of the cell morphology of AM-I-7wt were as follows. Under optimal culture conditions (22° C., 31 ppt salinity, pH 7.5 and an ample food supply) adult AM-I-7wt cells were amoeboid, actively moving plano-convex bodies, and generally 40 to 120 $\mu$m in diameter. The size of cells ranged from 10 to 1000 μm depending on cell age and recent feeding history. Active cells were generally found tightly attached to a substrate, feeding constantly and full of food particles which determined their coloration. The youngest cells were small, (10 to 20 μm in diameter) and flat with clear and stretched, hyaline, fan-like cytoplasm. After abundant feeding for 3 to 7 days, these cells grew into large plano-convex flat cells (40 to 120 μm) which were full of dense cytoplasm loaded with food vacuoles and storage granules. With respect to pseudopodia, AM-I-7wt had thin filipodia (2 to 4 μm wide, 5 to 30 μm long) apparently used for receiving sensory information, and wide lobopodia used for movement, and wide, clear areas of cytoplasm which extend while the cell is in motion. The amoeba also had cone-like protrusions (5 to 15 μm in length and 4 to 6 μm in width) on its surface from which the fine, needle-like filipodia extended The cell was enclosed in a clear fibrous envelope or "test".

AM-I-7wt moved slowly, from 10 to 15 μm per minute, and created cleared trails in its path by digesting the food upon which it was moving. The amoeba moved by extending a clear lobopod and streaming the granular cytoplasm into it.

On several occasions, the typically 2 μm wide, 15 to 20 μm long filipodia extending from the cytoplasm gradually changed their morphology. Within a few seconds, they were transformed into a 30 to 40 μm wide lobopodium which was then either retracted, widened further, or reshaped into a thin filipodium. Lobopodia were most common on flat, attached cells, where they were used for movement. The cone-like cytoplasmic protrusions moved with the surface membrane around the cell, changing their positions relative to each other and to the cell edges. It is not clear whether these were permanent structures or a transient formation of cell cytoskeleton. Lobopodia were round and were not observed in association with these cone-like protrusions. Light and electron microscope observations did not reveal a permanent structure in the cell membrane or in the cell test which corresponded to these cytoplasmic protrusions. Many other cell configurations for AM-I-7wt also existed. Among them were smooth, pointed, round or elongated cells.

Movement of cytoplasm between cells was observed in dense cultures, where physical contact between cells was common. Cells (60 μm) formed cytoplasmic bridges approximately 20 μm wide. Portions of the cytoplasm (approximately 20–30% of the cell volume) were observed as being exchanged simultaneously between the cells. The process lasted from 5 to 60 minutes. Cell membranes then formed replacing the bridge, and the cells moved away from each other. During such exchanges the two cells retained their individual morphology although their cytoplasm was bridged.

Cell Division

Two types of cell divisions were observed in AM-I-7wt: binary fission and multiple fission. Binary fission occurred in well-fed cultures, where cells larger than 60 μm diameter divided, forming two daughter cells not always identical in size nor having the same number of the nuclei. In preparation for division, opposite poles of one cell moved away from each other and a thin cytoplasmic bridge remained before the cells separated. Minimum cell size and the presence of a sufficient food supply were two necessary requirements for binary fission. Extremely large cells (500 to 1000 μm) went through a chain of binary fissions. As the oversized cells were dividing, and before the first division was completed, a second, third or fourth binary fission was initiated. Such large cells produced a chain of as many as eleven daughter cells during a division sequence that lasted ten minutes. Starved cells (without food for two weeks) retained their size for eight weeks and then shrank slowly as they became clear and barely recognizable. Feeding seaweed powder or algae to the starved cells restored their size to within a normal range (40 to 200 μm) within 3 to 10 days.

Multiple fission, a unique characteristic of AM-I-7wt was the second type of cell division. It was induced by exposing large cells (>60 μm) to fresh PES medium or seawater. Induction of multiple fission occurred two to five hours after the medium was replaced. Depending on culture conditions (age, pH, salinity or temperature) and the physiological state of the cells, multiple fission lasted from 5 to 48 hours. Each cell 60 to 1200 μm divided into from 10 to 260 or more progeny depending on the size of the original cell. During multiple fission the cells released the contents of their food vacuoles. The young cells (7 to 10 μm in diameter, slightly wrinkled and whitish beige) remained nearly motionless for 5 to 10 hours after division. Twenty hours later the cells were moving actively. They were clear and fan-like and stretched to 15 to 20 μm as they attached to the substrate. The cells' dense cytoplasm accumulated in one side of the cell, and a clear area with dense cytoplasmic ridges was formed in the direction of movement. Young, small cells started feeding as soon as they started moving. They also survived up to 8 weeks of starvation. Multiple fissions resulted in a 15 to 80 fold increase in progeny per division as compared to binary fission.

Nuclei

Nuclei which were stained by DAPI, fluoresced a bright blue color. As many as 450 nuclei were counted in large cells of 200 μm diameter. The number of nuclei was proportional to cell size. After multiple fission the nuclei were distributed between the progeny which contained 1 to 5 nuclei per cell. The nuclei were about 2 to 3 μm in diameter and evenly distributed in the cytoplasm between food vacuoles.

EXAMPLE III

Growth of AM-I-7wt on Various Food Substrates

AM-1-7wt isolated as described above was characterized by observing growth of the amoeba on different food sources. Feeding experiments were conducted using the following protocol. Food sources were used as a growth substrate and consisted of various seaweed cell wall extracts, seaweed, and unicellular algae, diatoms and dinoflagellates. The food was sterilized by axenic culturing (unicellular algae) or by autoclaving (seaweeds) before feeding, and was either inoculated with cultures of AM-I-7wt or added to previously established cultures of the amoeba.

Seaweed cell wall extracts (commercially available) were prepared as follows. Bacto-agar (DIFCO Laboratories, Detroit, Mich.) and agarose (Sigma Chemical Co., St. Louis, Mo.) were autoclaved in seawater and used at concentrations ranging from 0.1 to 1.5% (grams per 100 ml (g/100 ml)). Five ml of medium was poured into 4 cm diameter plastic petri dishes. The solutions were allowed to gel and were inoculated on the surface with approximately 20 AM-I-7wt cells (60 to 80 μm in diameter). In addition to gelled agar, foamed agar solutions were prepared by vigorously agitating warmed agar (40° C.) while chilling on ice to produce a foamed gel containing numerous trapped air bubbles. The foamed agar provides a porous substrate with larger surface area and an increased air supply for amoeba growth. Carrageenan (Irish moss, Type 1, Sigma), was autoclaved in seawater. A range of concentrations of Carrageenan from 0.5 to 2.5% (g/100 ml) was prepared and poured into dishes as above. Kelmar Algin (KR-2329-69, Kelco Company, San Diego, Calif.) a fucan (which is an extract from brown seaweeds such as Fucus and Sarqassum) was autoclaved in seawater and used in concentrations of 0.5 to 2.5% (g/100 ml).

In addition to seaweed cell wall extracts, live, axenic seaweed tissues, ½ to 1 cm in length (of varying widths) were used for feeding and were prepared as described by Polne-Fuller, et al., *Hydrobiologia,* 116/117: 308-313 (1984); Polne-Fuller, et al., *J. Phycol.,* 20: 609-616 (1984); and Polne-Fuller, et al., in Seaweed Cultivation for Renewable Resources, Gas Research Institute, Chicago, Ill. (1987), all of which are incorporated herein by reference. Cleaned seaweed tissues (250 mg) were placed in culture dishes containing seawater and approximately 20 amoebae cells were transferred onto the top of the seaweed tissues.

Autoclaved seaweed tissues were used for feeding large-scale (½ to 1 liter) amoebae cultures. Freshly collected seaweeds were cleaned of visible epiphytes and chopped using a standard kitchen blender for 2 minutes. The chopped tissues were rinsed in seawater and autoclaved for 20 minutes (500 g wet tissue/liter). For long periods of storage, seaweeds were air dried and ground in a coarse mill grinder (Arthur Thomas Corp., Philadelphia, Pa.) and stored dry. Before feeding, the ground seaweed (powder) was autoclaved in seawater (5 g/100 ml) and soaked for 24 hours, rinsed twice and re-sterilized in seawater.

In some cases tissues which were not digested well by the amoebae were autoclaved to soften the cell walls to determine whether the amoebae could then digest the algae.

Unicellular algae (listed below in Table I) were harvested by centrifugation and added to the amoebae as a thick suspension. Flagellated algae and dinoflagellates were frozen to stop motility before feeding to the amoebae. Diatoms were fed unfrozen since they moved slowly enough for the amoebae to capture.

AM-I-7wt was also cultured monoxenically with marine unicellular algae. The combined cultures required no additional feeding and were convenient for observations of amoeba movement, growth and feeding.

To count growing cultures, the bottoms of the dishes were marked with a 5 mm grid. The total number of cells was counted daily for two weeks. When the number of cells became too large to count, (i.e., greater than approximately 500 cells) 10 sample areas on the bottom of the grid were counted. An American Optics dissecting microscope at low magnification (30 X) was used for growth observations.

Coloration

The color of the AM-I-7wt amoebae and the apparent consistency of their cytoplasm observed visually and through a light microscope depended on the food source, as indicated by the observations of vacuole contents set forth in Table I. The contents of food vacuoles were observed using a compound light microscope. Multiple fission was used to induce release of vacuole content for observations of vacuole content outside of the amoeba cell. To obtain release of the contents of food vacuoles, the amoebae were induced to go through multiple fission by flooding with fresh seawater or PES salt medium. The cells stretched and divided into smaller cells (20 μm) within 24 hours. During the process of stretching and dividing the contents of the food vacuoles were released. The majority of food vacuoles released within 3 to 10 hours after induction of multiple fission. The contents of the vacuoles were then observed using a compound light microscope.

The results of growth of AM-I-7wt on various food substrates are shown in Table I.

TABLE I

| | Growth of AM-I-7wt | | |
|---|---|---|---|
| | Growth[a] (Cell Divisions/week) | | Vacuole[b] |
| Substrate | Live Tissue | Boiled | Contents |
| GREEN SEAWEEDS: | | | |
| Enteromorpha intestinalis | 0 | 1-2 | Green |
| Ulva angusta | 0-0.5 | 1-2 | " |
| Cladophora columbina | 0-0.6 | 2-3 | " |
| Chara ostralis | 0-1 | 1-2 | " |
| UNICELLULAR GREEN ALGAE: | | | |
| Chlamydomonas reinhardii | 9-11 | —[c] | Green |
| Dunaliella tertioleta | 7-10 | — | " |
| Platymonas subcordiformis | 8-9 | — | " |
| Carteria pallida | 8-9 | — | Gray-green |
| Nanocloris sp. | 9-10 | — | Orange-pink |
| Acetabularia mediterenea | 0-0.5 | — | Silver |
| BROWN SEAWEEDS: | | | |
| Macrocystis pyrifera gametophytes | 10-11 | — | Golden brown |
| Macrocystis pyrifera sporophytes | 8-10 | 9-10 | Brown |
| Laminaria farlowii sporophytes | 8-9 | 8-10 | Brown |
| Sargassum muticum | 5-7 | 6-7 | Dark brown |
| Sargassum filipendula | 7-8 | 7-8 | " |
| Sargassum natans | 7-8 | 7-8 | " |
| Sarqassum fluitans | 7-8 | 7-8 | " |
| Sargassum pteropleuron | 7-8 | 7-8 | " |
| Sargassum hystrix | 6-8 | 6-9 | " |
| Cystoseira osmundacea | 5-8 | 5-8 | " |
| Zonaria farlowii | 5-7 | 5-8 | Golden brown |
| RED SEAWEEDS: | | | |
| Porphyra perforata conchocelis | 3-5 | — | Purple-red |
| Porphyra perforata blades | 6-7 | 7-8 | Beige-red |
| Gracilaria sjoestedtii | 7-9 | 7-10 | Beige |
| Gracilaria andersonii | 8-10 | 8-10 | Beige |
| Gelidium robustum | 7-9 | 7-10 | Beige-red |
| Prionitis lanceolata | 8-9 | 8-10 | Beige-yellow |
| Eucheuma alvarezii | 8-9 | 8-10 | Beige-yellow |
| Gigartina exasperata | 8-9 | 7-10 | Beige-red |
| Gigartina pacilata | 8-9 | 8-10 | Beige-red |
| DIATOMS: | | | |
| Mixtures of pennate forms | 3-5 | — | Orange-yellow |
| DINO-FLAGELLATES: | | | |
| Gonyaulax polyhydra | 8-10 | — | Dark-brown |
| Peridinium social | 7-10 | — | Dark-brown |
| COMMERCIAL SEAWEED CELL WALL EXTRACTS: | | | |
| Alcin | — | 6-7 | Beige-brown |
| Aqar | — | 7-9 | Beige |
| Carraceenan | — | 7-9 | Beige |

TABLE I-continued

| | Growth of AM-I-7wt | | |
|---|---|---|---|
| | Growth$^a$ (Cell Divisions/week) | | Vacuole$^b$ |
| Substrate | Live Tissue | Boiled | Contents |
| Fucans | — | 7–9 | Dark golden brown |

$^a$Growth experiments were performed using cells 60 to 80 μm in diameter, which were dividing by binary fission.
$^b$Observations of vacuole contents were made using a light microscope as described above and recorded in terms of color.
$^c$— = Not tried.

Table I reveals that a variety of seaweed tissues, both alive and boiled, as well as plain agar, carrageenan, algin and fucans supported good growth of AM-I-7wt. Live green seaweeds (of the genera Enteromorpha, Ulva, Cladophora, Chara and Acetabularia) were the least edible. When supplied with live green seaweeds, the amoebae accumulated on the surfaces of the plant but did not penetrate the cuticles and walls, and growth did not occur. Boiled green seaweeds were more digestible and supported a marginal growth rate of from 1 to 2 cell divisions per week. In comparison, brown and red seaweeds supported good growth at 7 to 10 cell divisions per week. This suggests that while AM-I-7wt readily digests brown and red algae, it does not easily digest cell walls of green and higher plants.

Among the brown seaweeds, the Laminariales (e.g. Macrocystis supported the best amoeba growth. Macrocystis gametophytes were a preferred food type of the amoebae. Macrocystis and Laminaria sporophytes were also a preferred food, but required a longer period of digestion than the gametophytes. Sarqassum (Fucales), Cystoseira (Fucales), and Zonaria (Dictyotales) supported lower initial growth, but once the cultures were established the rate of cell divisions increased as compared to the number of cell divisions on the other food types.

Among the red seaweeds the agarophytes and carageenophytes were excellent food sources for AM-I-7wt. Gracilaria, Prionitis, and Eucheuma supported fast growth. Gelidium collected from the field and cleaned as described above supported growth of the AM-I-7wt amoeba, however, the outer branch envelopes or "cuticles" of laboratory grown Gelidium which were stored alive (dormant) for one year were not as easily penetrated and thus not digested well by the amoeba. Porphyra cuticles were also a difficult substrate for the amoebae to penetrate, although a week after inoculation AM-I-7wt was multiplying well between the cuticles of this plant. Boiled Porphyra cuticles were more accessible to but not totally digestible by AM-1-7wt.

Although the amoeba was able to digest several types of dinoflagellates such as Gonyaulax and Peridinium, it also was observed to grow in a symbiotic relationship with several species of symbiotic dinoflagellates within the group Zooxanthellae, for example—Symbiodinium sp. In this relationship, the amoeba divided by binary fission at a decreased rate (one division over from 3 to 5 weeks) but survived without additional food for over 18 months. The Zooxanthellae grew well in the presence of the amoeba and developed darker pigmentation then Zooxanthellae grown alone. In addition, the Zooxanthellae did not require replenishment of nutrients during the 18 months in culture with the amoeba.

Feeding Behavior

The AM-I-7wt amoeba engulfed food particles encountered in its path, engulfing smaller food particles and attaching to larger food matter, which was then digested by the amoeba. AM-I-7wt was also readily able to remove portions of live solid seaweed tissues and from various hard gels made from seaweed cell wall extracts. The amoebae cells crawled on many available substrates but clearly recognized edible from non-edible particles. The amoebae attached to but did not engulf glass beads unless the beads were coated with agar. On agar, each moving amoeboid cell created a tunnel which marked the cell's path in the agar. The amoeba left fecal pellets which were found not to contain proteins and which melted at 60° C., suggesting that the pellets contained agar components which were undigested by the amoeba. They did not engulf fecal pellets even when starved. The cells selectively collected digestible algal species from mixtures of algae.

If the amoebae were taking up the algae presented as food, the vacuoles should contain material having a color similar to the particular algae digested. This was confirmed by observations of the vacuole contents as indicated in Table I, where the color of the vacuole resembled the color of the algae source fed to the amoeba.

The complete digestion of the seaweed tissue by the amoeba, and the ability of the amoeba to subsist and grow on commercial cell wall extracts of red and brown seaweeds demonstrates the ability of AM-I-7wt to remove seaweed cell walls.

EXAMPLE IV

Partial Purification of Cell Wall Digesting Enzymes from AM-I-7wt

A partially purified enzyme mixture exhibiting algal cell wall digesting activity for use in degrading cell walls was obtained from AM-I-7wt as follows.

AM-I-7wt amoebae were grown on ten 20 cm$^2$ plastic dishes. The cells were detached and collected using a jet of water, such as that produced using a pipette. An agar surface cell scraper may also be used for collecting the cells. A thick cell suspension (containing approximately 10$^4$ cells/ml) was made using seawater and was kept on ice. To lyse the cells, the suspension was then placed in a glass bead homogenizer (Biospec Products, Bartlesville, OK) for ½ minute in 10 ml of phosphate buffer (pH 7.8) containing 0.1% bovine serum albumin (BSA) and 0.1 mM phenylmethylsulfonyl fluoride (PMSF). The solution was centrifuged (15,000 rpm for 10 minutes) and the supernatant collected. The supernatant was then fractionated using $(NH_4)_2SO_4$ and the 40 to 75% fraction was collected and resuspended in buffer.

The protein-containing fraction obtained as described above was tested for alginase activity as described by Nakada et al. *J. Biol. Chem.*, 242:845–851 (1967) incorporated by reference herein, and for carbohydrate degradation activity using the Anthron reaction described by Scott et al., *Anal Chem.* 25:1956 (1953) incorporated by reference herein. Briefly, the mixture was tested for the ability to degrade alginate, which is a gelling cell wall extract obtained from seaweeds known as kelps. The alginate will not absorb in the ultraviolet region until it is degraded. A 4% solution of alginate (Sigma) was prepared and mixed with approximately 20 μl of enzyme mixture prepared as described above, per ml of alginate. The absorbance of the solution under ultraviolet light was then examined at 230 nm using a spectrophotometer. The ability of the partially purified enzyme mixture from AM-I-7wt to degrade the alginate is demonstrated by the graph of FIG. 1 where absorbance increases over time as the alginate was degraded.

The above procedure produced approximately 10 ml of a concentrated, partially purified enzyme extract solution. The activity of the enzyme mixture may be expressed as a function of the alginate absorption. Thus the amount of enzyme mixture needed to increase the alginate absorption by one unit in one minute is one unit of activity. The enzyme mixture obtained as described above yielded approximately 32 units of activity per ml of solution.

Figure 2:
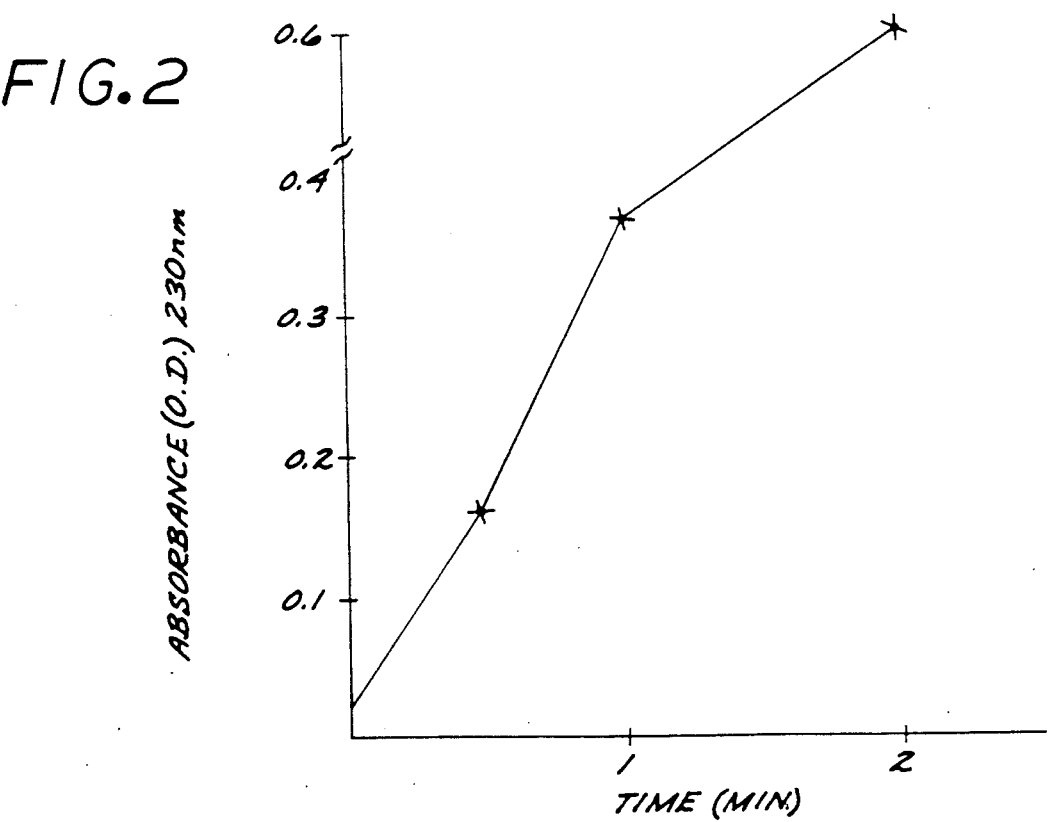
FIG. 2 is a graph showing the change in absorbance over time for alginate degradation by the partially purified enzyme mixture obtained from AM-I-7wt.

The ability of the partially purified enzyme mixture from AM-I-7wt to release sugars from intact tissues or commercial cell wall extracts was investigated using the colorimetric (purple color) Anthron reaction. FIG. 2 illustrates the carbohydrate degradation by the partially purified enzyme mixture. Absorbance increased over time as more sugar was released into the medium by the enzyme mixture.

The partially purified enzyme mixture may be conveniently stored for later use. 1 ml aliquots were stored at $-20°$ C. or lower for 3 months or more. An acetone powder was also prepared from the collected fraction by grinding seaweed in 100% cold acetone with ethyl ether to produce a powder which was dried and stored frozen at $-20°$ C. or lower for more than two months. Samples may then be thawed at room temperature, and buffer used to redissolve the powder.

The enzyme mixture isolated from AM-I-7wt using the procedure described above exhibited cell wall degrading activity at pHs from 5.4 to 8.5, and optimal activity at temperatures of from 22° C. to 26° C.

EXAMPLE V

Preparation of Seaweed Protoplasts using Partially Purified Cell Wall Digesting Enzymes from AM-I-7wt Seaweed tissue from *Sarcassum muticum* was cleaned as described by Polne-Fuller et al., (in: Seaweed Cultivation for Renewable Resources, Gas Research Inst., Chicago, Ill. (1987)), and was finely chopped using a sterile razor. The chopped tissue was immersed in the partially purified enzyme mixture prepared as described above in Example IV using 1 gram of chopped seaweed tissue per 3 ml (approximately 96 units of alginase activity) of extract. The solution was then agitated using a slow rotary shaker (Lab-Line Instruments, Melrose Park, Ill.) at 30 to 50 rpm for ½ to 2 hours. The progress of cell wall degradation to yield protoplasts was monitored using Anthron tests for sugar release as described above in Example IV and by microscopic observation of the degradation of the cell walls using calcofluor white stain (Sigma) which stains cellulose in cell walls a fluorescent green color. In addition, the presence of protoplasts was detected by testing for sensitivity to low osmoticums (cells with cell walls do not burst in low osmoticum solutions). Electrion microscopy may also be used to verify the presence of cells lacking cell walls. When "peak release" was obtained, defined as the time beyond which the number of protoplasts which are present decline as they become damaged by the presence of the enzymes, (approximately ½ to 2 hours), single cells and protoplasts were manually removed and rinsed to remove the enzymes to stop damage to the protoplasts, using gradual dilutions in buffer and 0.6 M sorbitol. Other solutes such as sucrose or salts may be used depending on the algae selected and on the type of cell released.

Separation of protoplasts and cells from the algal tissue may be accomplished using nylon screens. Gentle centrifugation and/or liquid interphase may be used to retrieve the cells from solution depending on cell size and density. The remaining seaweed tissue was returned to the partially purified enzymes or placed in a fresh preparation of enzymes if further cell wall degradation was desired.

If the seaweeds are tropical the procedure for obtaining protoplasts may be done at room temperature for from ½ to 24 hours. Cold water habitat seaweeds should be incubated in the cold (12 to 18° C.) for from 2 to 24 hours depending on the plant material).

Using the above procedure, viable protoplasts ($10^4$/g tissue) were obtained from Sarqassum muticum. $10^4$ to $10^8$ viable protoplasts/g of tissue have been obtained from a variety of algae types.

EXAMPLE VI

Isolation of a Plastic Degrading Amoeba, AM-I-7PL

AM-I-7wt served as the parent organism from which the mutant amoeba AM-I-7PL, capable of degrading plastics, was derived.

AM-I-7wt cultures which were identified as capable of digesting seaweed cell walls, obtained as described above, were placed in sterile seawater and the amoebae were mutated by exposure to a germicidal lamp (American Ultraviolet Co., Chatham, N.J.) 27 cm away from the source for 15 minutes. Surviving cells were flooded by fresh PES medium. Initial isolation of the plastic degrading strain was done using sheets of the commercial plastic wrap Saran Wrap ® composed of the chlorinated hydrocarbons polyvinylchloride (PVC) and polyvinylidin di-chloride (PVDCl) as a carbon source. Autoclaved plastic bags made of polypropylene were also used as a sole carbon food source.

Observations of morphology, growth and feeding similar to those performed on AM-I-7wt were also conducted on AM-I-7PL. The morphology of AM-I-7PL appeared indistinguishable from that of AM-I-7wt as determined by visual and light microscope observation. The amoeba was capable of surviving on plastics as a sole carbon source as evidenced by its continued ability to undergo cell divisions and the physical degradation of the plastics over time, as evidenced by holes and overall deterioration of the plastics. With plastic as the only carbon source, with no vitamins or amino acids available, the cell divisions of the amoeba were as much as 30 to 60 fold lower than the cell divisions on algae food sources.

The feeding behavior of the AM-I-7PL was also similar to that of AM-I-7wt; AM-I-7PL engulfed smaller plastic particles and attached to larger particles. AM-I-7PL demonstrated optimal growth on algal tissue rich in nutrients as shown in Table II and described further below.

Based on these observations, AM-I-7PL was identified as a new strain of amoeba. A culture of the mutant strain has been deposited with the ATCC and accorded accession number ATCC 40319.

The following example demonstrates the ability of AM-I-7PL to survive on a variety of food substrates including complex hydrocarbons such as wax, paraffin, plastic wrap, polyethylene, polypropylene, polyvinylchloride and polyvinylidin di-chloride.

EXAMPLE VII

Characterization of AM-I-7PL

Studies were performed to determine the ability of the mutant organism AM-I-7PL to survive on various food substrates. Pulverized polyvinylchloride and polyvinylidin di-chloride were sterilized in seawater using an autoclave and were placed in petri dishes containing PES medium at 22° C. and inoculated with approximately 100 to 200 cells of AM-I-7PL per dish.

Seaweeds were prepared as described above in Example III. All other substrates were sterilized either by autoclave or in 70% ethanol and placed in plastic dishes with the amoeba. AM-I-7PL cell viability was determined over a 6 month period by measuring the rates of cell division and observing the content of food vacuoles. Cell divisions were determined by counting the number of cells in each petri dish. The results of these studies are depicted in Table II.

TABLE II

GROWTH OF AM-I-7PL ON VARIOUS SUBSTRATES

| Substrate | Cell Divisions/Weeks[a] | Vacuole[b] Contents |
|---|---|---|
| SYNTHETICS: | | |
| Paraffin | 1-3 | - clear, oily |
| Wax | 1-4 | - clear |
| Polyethylene | 2-3 | - clear |
| Polypropylene | 0-2 | - clear |
| Plastic Wrap | 1-2 | - granular, beige |
| Polyvinyl chloride | 0-0.5 | - granular, golden |
| Polyvinylidin di-chloride | 0.5-1.5 | |
| SEAWEEDS [ALGAE]: | | |
| Brown algae | 8-10 | - granular, brown |
| Red algae | 8-10 | - opaque, beige |
| Unicellular green algae | 9-11 | - granular, green |
| PLANT EXTRACTS: | | |
| Methyl cellulose | 5-7 | - opaque, whitish |
| Carboxy methyl cellulose | 6-9 | - opaque, whitish |
| Corn starch | 3-5 | - opaque, whitish |
| Inolin | 4-6 | - clear |
| Carrageenan | 7-9 | - opaque, beige |
| Fucans | 7-9 | - granular, dark golden brown |
| Dextran | 3-7 | - clear |
| Alginate | 6-9 | - opaque, beige |
| Agar | 5-8 | - opague, beige |
| SUGARS: | | |
| Fructose | 1-4 | - opaque, whitish |
| Fucose | 2-4 | - clear |
| Galactose | 2-3 | - granular, yellow |
| Sucrose | 0-3 | - clear |
| Glucose | 1-3 | - clear, silver tint |
| Sorbitol | | |
| OTHER CHEMICALS: | | |
| Ficol | 1-2 | - clear |
| Trichloroacedic acid (TCA) | 0-3 | - clear |
| Sodium Acetate | 0-2 | - clear |
| Teflon | 0 | - —[c] |

[a]Growth experiments were performed using cells 40 to 80 μm in diameter dividing by binary fission.
[b]Observations were made after obtaining release of vacuolar contents, using a light microscope (400 X).
[c]The teflon was not digested by the amoeba.

The data in Table II demonstrate that AM-I-7PL degrades complex hydrocarbons including plastics containing halogenated hydrocarbons as indicated by its ability to survive on such materials as a sole food source. When grown on seaweeds or algae, AM-I-7PL exhibits temperature and salinity tolerance similar to AM-I-7wt (4° to 32° C. and 2.8 to 4.5 ppt salinity) and binary fission rates of from 1 to 2 per day up to approximately 10 divisions per week. However, when AM-I-7PL was grown on plastics as a sole source of carbon for a period of time greater than three months, its temperature tolerance narrowed to from 10° to 24° C. and its growth rates were reduced to one division per 3 to 6 weeks. Nutritional supplementation with vitamins and amino acids (using a yeast extract and a casein hydrolysate) increased cell division when the cells were grown on plastics.

AM-I-7PL was also capable of digesting algae cell walls as illustrated by its ability to thrive when fed brown and red seaweed and unicellular green algae, including diatoms and dinoflagelates as a sole food source.

EXAMPLE VIII

Partial Purification of Plastic Degrading Enzymes from AM-I-7PL

A partially purified enzyme mixture capable of degrading complex hydrocarbons is obtained from the amoeba AM-I-7PL using the procedures described above in Example IV for isolating enzymes from AM-I-7wt. The mixture is then tested for activity, for example alginase activity and for carbohydrate degradation to indicate algae cell wall digestion, as described above for AM-I-7wt. In addition, the plastic-degrading activity of the partially purified enzymes from AM-I-7PL is examined using a complex hydrocarbon material as a food source containing radioactively labeled hydrocarbon chains, for example the plastic polyvinyl chloride labeled with C14. Alternatively, the food source is labeled with a fluorescent agent. The activity of the enzymes is then determined using the label to detect the presence of degraded hydrocarbon chains, for example using mass spectrophotometry.

From the descriptions in the literature, and based on the above-described characteristics, AM-I-7wt and AM-I-7PL resemble *Amoeba tentaculata* (Gruber, Z. Wiss. Zool. XXXVI, p. 459, pl. XXX (1881)), *Pontifex maximum* (Schaeffer, *Publ. Carneqie Institution of Washington*, #345 (1926), or the smooth form (gamont) of *Trichosphaerium platyxyrum* (Angell, Jr., *Protozool.*, 23(3): 357-364 (1976)). All three have been previously suggested to be a single organism. Page, *Cambridqe Inst. of Terrestrial Ecology*, p. 45-47 (1983). Although AM-I-7wt and AM-I-7PL resemble the above organisms, particularly Trichosphaerium, they appear to be distinct based on a comparison of several features as summarized in Table III below.

TABLE III

COMPARISON BETWEEN AM-I-7wt, AM-I-7PL AND OTHER SIMILAR AMOEBAE

| Feature | AM-I-7wt/ and AM-I-7PL | Trichosphaerium platyxyrum | Pontifex maximum/ Amoeba tentaculata |
|---|---|---|---|
| 1. Spicules | — | + | + |
| 2. Diameter | 20-5000 μm | 26-110 μm | 35-100 μm |
| 3. No. of nuclei | 2->800 | 9-56 | 26-144 |
| 4. Size of nuclei | 2 μm | ? | 6 μm |
| 5. Food[1] | | Euglena, Dunaliella | rice grain |
| 6. Symbiosis (with zooxanthellae) | + | ? | ? |
| 7. Salinity | (3-4.5 g/l) | 3 g/l | ? |
| 8. Multiple fission | + | — | — |
| 9. Binary fission | + | + | + |

TABLE III-continued
COMPARISON BETWEEN AM-I-7wt, AM-I-7PL AND OTHER SIMILAR AMOEBAE

| Feature | AM-I-7wt/ and AM-I-7PL | Trichosphaerium platyxyrum | Pontifex maximum/ Amoeba tentaculata |
|---|---|---|---|
| 10. Binary fission upon starvation | + | – | ? |
| 11. Temperature | 4–32° C. | 22–29° C. | ? |
| 12. Subculture | 6 weeks | 2–5 days | ? |
| 13. Gametogenesis | – | + | + |
| 14. *Filipodia/ dactylopodia* | + | – | – |
| 15. Filipodia used for movement | + | – | – |
| 16. Lobopodia | + | + | + |
| 17. Lobopodia used for feeding and movement | + | + | + |
| 18. Test | + | + | + |
| 19. Protrusions on outer cell membrane | + | + | ? |

¹seaweeds, walls, diatoms, dinoflagellates, green unicells, sugars, methyl cellulose, other complex carbohydrate polymers. (AM-I-7PL attack complex hydrocarbons includinq paraffin, PVC and PVDC1 as well)
+ = feature present
– = feature absent
? = unreported As can be seen from Table III the amoebae similar to AM-I-7wt and AM-I-7PL perform binary fission, have filipodia and lobopodia, move by the lobopodia, and all have a test. However, AM-I-7wt and AM-I-7PL appear to differ in the absence of spicules; larger maximum cell size attained; larger number of nuclei per cell; small size of nuclei; ability to consume and survive on a wide range of food types; ability to create a symbiotic relationship with certain dinoflagellates; multiple fission; and binary fission when food is in short supply; lack of gametogenesis and use of filipodia for movement of the cell body.

Both AM-I-7wt and AM-I-7PL thus provide easily cultured microorganisms for digesting seaweed cell walls. The amoeba are preferably cultured under conditions of from 5° C. to 25° C. and preferably from about 20° C. to 25° C. at a pH of from 6 to 9 and preferably 7 to 8, under aerobic conditions. Artificial seawater may be used in place of natural seawater to culture both AM-I-7wt and AM-I-7PL. For example, "Instant Ocean ®" available from Aquarium Systems, Inc. (Mentor, Ohio), Tropic Marine Salts (Aquarientechnik, Wartenberg, Germany) and Gulf aquarium salt (Weco Products, Long Beach, Calif.) support continued growth and multiple fission when used at from 3 to 4.5 g/100 ml of water. They may be employed alone or in combination, or by including other microorganisms, to remove cell walls from seaweeds for the generation of protoplasts.

In addition, AM-I-7PL may be useful for the biological treatment of plastic and plastic by-products to reduce environmental pollution.

The cell wall-and plastic-degrading enzymes may be isolated in partially purified form from the amoebae, as described herein, and may be used in methods to degrade cell walls or complex hydrocarbons. The partially purified enzyme mixtures may be further purified to isolate and characterize individual enzymes capable of degrading specific components of cell walls and complex hydrocarbons.

In the above manner, algal cell walls, complex hydrocarbons including plastics and the like which have been previously considered to be difficult to degrade, or are nonbiodegradable, can be advantageously treated using the organisms described herein.

As will be apparent to those skilled in the art in which the invention is addressed, the present invention may be embodied in forms other than those specifically disclosed above without departing from the spirit or potential characteristics of the invention. It is contemplated that derivatives and equivalents of AM-I-7wt and AM-I-7PL may be obtained from these amoebae without departing from the scope of the present invention. Particular embodiments of the present invention described above are therefore to be considered in all respects as illustrative and not restrictive. The scope of the present invention is as set forth in the appended Claims and equivalents thereof rather than being limited to the examples contained in the foregoing description.

We claim:

1. A biologically pure culture of multinucleated marine amoeba capable of digesting algal cell walls having the identifying characteristics of ATCC 40318.

2. A method of digesting algal cell walls comprising contacting algae with the biologically pure culture of marine amoeba of claim 1 for a time and under conditions sufficient to degrade the algal cell walls.

3. The method of claim 2 wherein said algae is selected from the group consisting of red and brown seaweed, unicellular green algae and diatoms and dinoflagellates.

4. A biologically pure multinucleated marine amoeba having the identifying characteristics of ATCC 40319, said amoeba being capable of digesting algal cell walls and having the further capacity to degrade paraffin, wax, polyethylene, polypropylene, polyvinyl chloride polyvinylidene di-chloride and mixtures thereof.

5. A method of digesting algal cell walls comprising contacting algae with the biologically pure culture of marine amoeba of claim 4 for a time and under condition sufficient to degrade the algal cell walls.

6. A method of degrading a complex hydrocarbons comprising contacting a complex hydrocarbon capable of degradation by the biologically pure culture of marine amoeba of claim 4 with said amoeba for a time and under conditions sufficient to degrade the complex hydrocarbon.

7. The method of claim 6 wherein the complex hydrocarbon is selected from the group consisting of paraffin, wax, polyethylene, polypropylene, polyvinyl chloride, polyvinylidene di-chloride and mixtures thereof.

8. The method of claim 6 wherein the complex hydrocarbon is a halogenated hydrocarbon.

9. Partially purified enzyme or enzymes capable of degrading a complex hydrocarbon selected from the group consisting of paraffin, wax, polyethylene, polypropylene, polyvinyl chloride, polyvinylidene dichloride and mixtures thereof, wherein said enzymes exist in the amoeba of claim 4.

10. A method for degrading a complex hydrocarbon comprising contacting said complex hydrocarbon capable of degradation by the partially purified enzymes of claim 9 with said enzymes for a time and under conditions sufficient to degrade the complex hydrocarbon.

11. The method of claim 10 wherein the complex hydrocarbon is a halogenated hydrocarbon.

* * * * *

UNITED STATES PATENT AND TRADEMARK OFFICE
CERTIFICATE OF CORRECTION

PATENT NO. : 5,051,365

DATED : September 24, 1991

INVENTOR(S) : MIRIAM POLNE-FULLER

It is certified that error appears in the above-identified patent and that said Letters Patent is hereby corrected as shown below:

Column 8, Table I under heading RED SEAWEEDS, delete "pacilata" and insert therefor --papilata--.

Column 8, Table I under heading COMMERCIAL SEAWEED CELL WALL EXTRACTS, please delete "Alcin" and insert therefor --Algin--.

Column 8, Table I under heading COMMERCIAL SEAWEED CELL WALL EXTRACTS, please delete "Aqar" and insert therefor --Agar--.

Column 8, Table I under heading COMMERCIAL SEAWEED CELL WALL EXTRACTS, please delete "Carraceenan" and insert therefor --Carrgeenan--.

Column 14, line 40 please delete "Carneqie" and insert therefor --Carnegie--.

Column 16, line 42 (Claim 6) please delete "hydrocarbons" and insert therefor --hydrocarbon--.

Signed and Sealed this

Seventh Day of June, 1994

Attest:

BRUCE LEHMAN

*Attesting Officer*  Commissioner of Patents and Trademarks